United States Patent
Katou et al.

(10) Patent No.: US 9,199,901 B2
(45) Date of Patent: Dec. 1, 2015

(54) METHOD FOR PRODUCING MEDIUM-MOLECULAR-WEIGHT POLYALKYLENEOXIDE

(71) Applicant: Sumitomo Seika Chemicals Co., Ltd., Kako-gun (JP)

(72) Inventors: Makoto Katou, Chiyoda-ku (JP); Toru Ido, Himeji (JP); Masahiro Gotou, Himeji (JP)

(73) Assignee: Sumitomo Seika Chemicals Co., Ltd., Kako-gun (JP)

( * ) Notice: Subject to any disclaimer, the term of this patent is extended or adjusted under 35 U.S.C. 154(b) by 0 days.

(21) Appl. No.: 14/361,888

(22) PCT Filed: Nov. 22, 2012

(86) PCT No.: PCT/JP2012/080337
§ 371 (c)(1),
(2) Date: May 30, 2014

(87) PCT Pub. No.: WO2013/080888
PCT Pub. Date: Jun. 6, 2013

(65) Prior Publication Data
US 2015/0141705 A1   May 21, 2015

(30) Foreign Application Priority Data

Nov. 30, 2011 (JP) .................................. 2011-262677

(51) Int. Cl.
*C07C 41/18* (2006.01)
*C08G 65/10* (2006.01)
*C07C 43/04* (2006.01)
*C07C 43/11* (2006.01)

(52) U.S. Cl.
CPC .................. *C07C 41/18* (2013.01); *C07C 43/04* (2013.01); *C07C 43/11* (2013.01); *C08G 65/10* (2013.01)

(58) Field of Classification Search
CPC .......... C07C 41/18; C07C 43/04; C07C 43/11
See application file for complete search history.

(56) References Cited

U.S. PATENT DOCUMENTS

| | | | |
|---|---|---|---|
| 2,982,742 A | 5/1961 | Smith et al. | |
| 4,200,704 A * | 4/1980 | Stanley et al. | 525/409 |

FOREIGN PATENT DOCUMENTS

| | | |
|---|---|---|
| JP | 55-142027 A | 11/1980 |
| JP | 56-24420 A | 3/1981 |
| JP | 2002-105195 A | 4/2002 |
| JP | 2002-105196 A | 4/2002 |
| JP | 2002105196 A * | 4/2002 |
| JP | 2011-215377 A | 10/2011 |

OTHER PUBLICATIONS

International Search Report issued Feb. 19, 2013 in PCT/JP2012/080337.

* cited by examiner

*Primary Examiner* — Sudhakar Katakam
(74) *Attorney, Agent, or Firm* — Oblon, McClelland, Maier & Neustadt, L.L.P.

(57) ABSTRACT

A method for producing a medium-molecular weight polyalkylene oxide having a viscosity-average molecular weight of from 100,000 to 2,500,000, including heat-treating a polyalkylene oxide having a viscosity-average molecular weight of 3,000,000 or more at a temperature of from 30° to 70° C. in an aliphatic hydrocarbon solvent having a dissolved oxygen concentration of 0.5 mg/L or more, in the presence of a radical initiator in an amount of from 0.001 to 1 part by mass, based on 100 parts by mass of the polyalkylene oxide, and thereafter adding an antioxidant to a mixture in an amount of from 0.001 to 5 parts by mass, based on 100 parts by mass of the polyalkylene oxide to remove the solvent. According to the method of the present invention, a medium-molecular weight polyalkylene oxide having a viscosity-average molecular weight of from 100,000 to 2,500,000 which has excellent storage stability can be industrially obtained without subjecting to a gamma-ray irradiation treatment.

9 Claims, No Drawings

METHOD FOR PRODUCING MEDIUM-MOLECULAR-WEIGHT POLYALKYLENEOXIDE

TECHNICAL FIELD

The present invention relates to a method for producing a medium-molecular weight polyalkylene oxide. More specifically, the present invention relates to a method for producing a medium-molecular weight polyalkylene oxide, for use in thickeners for paper making, ceramic binders, aids in suspension polymerization, raw materials for pharmaceutical formulations, and the like.

BACKGROUND ART

Among the polyalkylene oxides, a water-soluble polymer polyethylene oxide has been used in diversified applications, such as thickeners for paper making, ceramic binders, aids in suspension polymerization, and raw materials for pharmaceutical formulations.

This polyethylene oxide is a linear polymer, so that much of the polymer physical properties are dominated by its molecular weight. Therefore, commercially available polyethylene oxides are mostly classified into grades according to their molecular weights.

The molecular weight of the polyethylene oxide is generally within the range of from 100,000 to 10,000,000 or so, and it is considered to be difficult to economically produce polyethylene oxides having molecular weights of from 100,000 to 2,500,000 or so out of those polyethylene oxides by direct polymerization in a high yield. As a method for obtaining a polyethylene oxide having a molecular weight of from 100,000 to 2,500,000 or so, a method including degrading a polyethylene oxide having a molecular weight of 3,000,000 or more produced by polymerization by gamma-ray irradiation has been generally known. However, the gamma-ray irradiation can only be applied in a publicly approved facility, in a limited area, so that there are some disadvantages in transportation costs and complicatedness of quality control. Further, the polyethylene oxide after the gamma-ray irradiation has some disadvantages of being poor in storage stability, lowering its molecular weight with the passage of time.

In view of the above, various studies have been made on molecular weight control with means other than the gamma-ray irradiation. As the degradation treatment other than the gamma-ray irradiation, the following methods have been reported.

For example, in Patent Publication 1, a peroxide is added to a polyethylene oxide, and the mixture is then heat-treated, thereby lowering an aqueous solution viscosity of a polyethylene oxide. In addition, in Patent Publication 2 it is mentioned that heat treatment is carried out under an oxygen concentration of from 10 to 500 ppm in addition to the same conditions as above, whereby the amount of a peroxide or a radical initiator can be reduced to from 0.5 to 5% by mass of the amount, based on the polyethylene oxide. In Patent Publications 3 and 4, a silicon dioxide powder is used as an anti-caking agent together with a polyethylene oxide, an aliphatic hydrocarbon, and a radical initiator.

PRIOR ART REFERENCES

Patent Publications

Patent Publication 1: U.S. Pat. No. 2,982,742
Patent Publication 2: U.S. Pat. No. 4,200,704
Patent Publication 3: Japanese Patent Laid-Open No. Sho-56-24420
Patent Publication 4: Japanese Patent Laid-Open No. Sho-55-142027

SUMMARY OF THE INVENTION

Problems to be Solved by the Invention

However, any one of the patent publications do not mention on the stability of the polyethylene oxide after the treatment in detail.

An object of the present invention is to provide a method for producing a medium-molecular weight polyalkylene oxide having excellent storage stability.

Means to Solve the Problems

The present invention relates to a method for producing a medium-molecular weight polyalkylene oxide having a viscosity-average molecular weight of from 100,000 to 2,500,000, including heat-treating a polyalkylene oxide having a viscosity-average molecular weight of 3,000,000 or more at a temperature of from 30° to 70° C. in an aliphatic hydrocarbon solvent having a dissolved oxygen concentration of 0.5 mg/L or more, in the presence of a radical initiator in an amount of from 0.001 to 1 part by mass, based on 100 parts by mass of the polyalkylene oxide, and thereafter adding an antioxidant to a mixture in an amount of from 0.001 to 5 parts by mass, based on 100 parts by mass of the polyalkylene oxide to remove the solvent.

Effects of the Invention

According to the method of the present invention, a medium-molecular weight polyalkylene oxide having a viscosity-average molecular weight of from 100,000 to 2,500,000 which has excellent storage stability can be industrially obtained without subjecting to a gamma-ray irradiation treatment.

MODES FOR CARRYING OUT THE INVENTION

In the method for producing a medium-molecular weight polyalkylene oxide of the present invention, a first step includes heat-treating a polyalkylene oxide having a viscosity-average molecular weight of 3,000,000 or more at a temperature of from 30° to 70° C. in an aliphatic hydrocarbon solvent having a dissolved oxygen concentration of 0.5 mg/L or more, in the presence of a radical initiator in an amount of from 0.001 to 1 part by mass, based on 100 parts by mass of the polyalkylene oxide.

The polyalkylene oxide usable in the present invention includes, for example, those containing ethylene oxide as one component, including an ethylene oxide homopolymer polyethylene oxide; and copolymers of ethylene oxide and other alkylene oxides. Other alkylene oxides mentioned above include, for example, propylene oxide, 1,2-epoxybutane, 2,3-epoxybutane, epichlorohydrin, epibromohydrin, trifluoromethylethylene oxide, cyclohexene oxide, styrene oxide, methyl glycidyl ether, allyl glycidyl ether, phenyl glycidyl ether, glycidol, glycidyl acrylate, butadiene monoxide, butadiene dioxide, and the like.

Among them, a polyethylene oxide, or an ethylene oxide/propylene oxide copolymer is preferably used, from the viewpoint of easy production, thereby obtaining a useful medium-molecular weight polymer. Here, the content of ethylene oxides in the above-mentioned copolymer is not particularly limited, and it is preferable that the content is usually 70% by mol or more.

The viscosity-average molecular weight of the polyalkylene oxide is 3,000,000 or more, preferably from 3,000,000 to 20,000,000, more preferably from 3,000,000 to 10,000,000, even more preferably from 4,500,000 to 8,500,000, and still even more preferably from 5,200,000 to 8,500,000. When the viscosity-average molecular weight of the polyalkylene oxide is less than 3,000,000, it is difficult to control the degradation during the heat treatment, so that there is a risk of not being able to obtain a polyalkylene oxide having an intended molecular weight. When the viscosity-average molecular weight of the polyalkylene oxide exceeds 20,000,000, the reaction would be carried out for a long period of time, thereby making production efficiency poor, thereby having a risk of not being industrially suitable.

The method for producing a polyalkylene oxide is not particularly limited, and a known method can be utilized. For example, a polyethylene oxide or an ethylene oxide/other alkylene oxide copolymer can be produced by polymerizing ethylene oxides or copolymerizing ethylene oxide and other alkylene oxides, in the presence of an alkali or a metal catalyst.

As the aliphatic hydrocarbon solvent usable in the present invention the aliphatic hydrocarbon may be a single solvent or a mixed solvent without particular limitations, so long as the aliphatic hydrocarbon solvent is in a liquid state under operable treatment conditions, and the solvent substantially does not dissolve a polyalkylene oxide. An aliphatic hydrocarbon having from 5 to 8 carbon atoms is preferred, from the viewpoint of reducing the residual solvent after drying. The aliphatic hydrocarbon having from 5 to 8 carbon atoms includes, for example, n-pentane, 2-methylpentane, n-hexane, cyclohexane, 2-methylhexane, 3-methylhexane, n-heptane, and the like. The amount of the aliphatic hydrocarbon solvent used is not particularly limited, so long as the aliphatic hydrocarbon solvent allows homogenous dispersion of a polyalkylene oxide, and maintains a flowable state under the treatment conditions. The amount of the aliphatic hydrocarbon solvent used is preferably 300 parts by mass or more, and more preferably from 400 to 500 parts by mass, based on 100 parts by mass of the polyalkylene oxide.

In the present invention, the polyalkylene oxide is heat-treated in an aliphatic hydrocarbon solvent having a dissolved oxygen concentration of 0.5 mg/L or more, preferably from 0.5 to 20 mg/L, and more preferably from 0.5 to 5 mg/L. In the present invention, a radical is generated on a carbon atom of the polyalkylene oxide by a radical initiator described later, and thereafter oxidation by oxygen takes place to form a peroxy radical. It is deduced that the degradation of the polyalkylene oxide takes place with this peroxy radical as a starting point. Therefore, when the dissolved oxygen concentration is lower than 0.5 mg/L, there is a risk that oxidation is not sufficient. In addition, there are no particular problems so long as the dissolved oxygen concentration is equal to or lower than a saturated concentration, and it is desired that the dissolved oxygen concentration is 20.0 mg/L or less. The method of adjusting a dissolved oxygen concentration of the aliphatic hydrocarbon is not particularly limited, and a concentration can be adjusted to a given dissolved oxygen concentration by, for example, a method of aerating nitrogen containing a given level of an oxygen concentration into a system, or a method of bubbling nitrogen containing a given level of an oxygen concentration in a solvent. Here, the dissolved oxygen concentration is measured with a dissolved oxygen meter, e.g., one manufactured by CENTRAL KAGAKU CORPORATION, portable digital DO/O2/TEMP meter, Model UC-12-SOL.

As the radical initiator usable in the present invention, a radical initiator of which 10-hour half-life temperature is 70° C. or lower is preferably used. The 10-hour half-life temperature as referred to herein is a temperature at which a concentration of the radical initiator is reduced to a half of the initial concentration in 10 hours. Here, since a melting initiation temperature of the polyethylene oxide is 63° C. or so, it is preferable as an index for selecting a radical initiator suitable for a heat treatment at low temperatures. The radical initiator that satisfies the conditions includes azonitriles such as 2,2'-azobis(4-methoxy-2,4'-dimethylvaleronitrile) and 2,2'-azobis-(2,4'-dimethylvaleronitrile); azoamidines such as 2,2'-azobis[N-(carboxymethyl)-2-methyl-propionamidine] tetrahydrate and 2,2'-azobis(2-amidinopropane) dihydrochloride; azoimidazolines such as 2,2'-azobis[2-(2-imidazolin-2-yl)propane]dihydrochloride and 2,2'-azobis[2-(2-imidazolin-2-yl)propane]disulfate dihydrate; peroxides (peroxides in phonetics) such as benzoyl peroxide and lauroyl peroxide; sulfur-containing compounds such as tetramethylthiuram disulfide; oxidizing agents such as potassium permanganate; organometallic compounds such as alkylaluminum and alkylzinc; and the like. Among them, the azonitriles such as 2,2'-azobis-(2,4'-dimethylvaleronitrile) are preferably used.

The existing amount of the radical initiator is from 0.001 to 1 part by mass, and preferably from 0.01 to 0.5 parts by mass, based on 100 parts by mass of the polyalkylene oxide. When the amount of the radical initiator is less than 0.001 parts by mass, the degradation speed is very slow, so that an intended molecular weight cannot be obtained, or would undesirably need a long treatment time. In addition, when the amount exceeds 1 part by mass, the degradation speed is very fast, so that it is difficult to control to an intended molecular weight, and at the same time excess radical initiators remain in large amounts, thereby having a risk of giving disadvantageous influences to storage stability of the polyalkylene oxide after the treatment.

The heating temperature for heat-treating the polyalkylene oxide is from 30° to 70° C., preferably from 30° to 60° C., and more preferably from 35° to 50° C. When the heating temperature is lower than 30° C., the degradation speed is very slow, so that a treatment time would be long in order to obtain an intended molecular weight, and if the time is to be shortened, a radical initiator needs to be used in large amounts, so that an excess radical initiator would remain in large amounts, thereby having a risk of giving disadvantageous influences to storage stability of the polyalkylene oxide after the treatment. In addition, when the heating temperature is at a high temperature exceeding 70° C., the polyalkylene oxide itself is likely to be agglomerated, forming a lumpy mass, so that there is a risk that the polyalkylene oxide cannot be obtained to be used in manufactured articles.

The treatment time cannot be unconditionally determined because the treatment time is a function of the heating temperature, and it is preferable that the treatment time is usually from 1 to 5 hours or so. When the heating temperature is high, the treatment time would be shorter, thereby making it more economically advantageous.

In the present invention, solid particle materials may be added during the heat treatment of the polyalkylene oxide. For example, in a case of a polyethylene oxide, a melting initiation temperature is 63° C. or so, so that when the treatment temperature is raised, the polyethylene oxide is likely to be agglomerated, and lumpy masses are likely to be formed.

When the heat-treatment temperature is from 40° to 50° C., the treatment can be carried out without worsening the shape of the polyethylene oxide even when solid particle materials are not added. However, if the treatment is tried to be carried out at a temperature higher than 55° C. in a short time period, not only the materials are granulated, thereby losing the shape, but also lumpy masses are formed, so that there is a risk that the polyalkylene oxide cannot be obtained to be used in a manufactured article. Therefore, it is preferable that the solid particle materials are added to inhibit agglomeration. The solid particle materials are not particularly limited, so long as the materials can inhibit agglomeration of the polyalkylene oxide, and the solid particle materials include inorganic materials such as silica, alumina, titania, talc, clay materials, and graphite; and organic materials such as maize powders. The amount of the solid particle materials is preferably within the range of from 0.5 to 5 parts by mass, and more preferably within the range of from 1 to 3 parts by mass, based on 100 parts by mass of the polyethylene oxide.

In the present invention, a second step including adding an antioxidant to a treated liquid mixture in which the heat treatment in the first step mentioned above is terminated to remove the solvent.

The antioxidant is not particularly limited, so long as the antioxidant is dissolved in the aliphatic hydrocarbon. It is preferable that the antioxidant is at least one member selected from the group consisting of phenol-based antioxidants, amine-based antioxidants, organosulfur-based antioxidants, and phosphorus-based antioxidants, from the viewpoint of radical scavenging property. The phenol-based antioxidants include dibutylhydroxytoluene (BHT), dibutylhydroxyanisole (BHA), octadecyl-3-(3,5-di-tert-butyl-4-hydroxyphenyl)propionate, 2,2'-methylenebis(4-methyl-6-tert-butylphenol), 2-tert-butyl-6-(3-tert-butyl-2-hydroxy-5-methylbenzyl)-4-methylphenyl acrylate, 2-[1-(2-hydroxy-3,5-di-tert-pentylphenyl)ethyl]-4,6-di-tert-pentylphenyl acrylate, 4,4'-butylidenebis(3-methyl-6-tert-butylphenol), 4,4'-thiobis(3-methyl-6-tert-butylphenol), tetrakis[methylene-3-(3,5-di-tert-butyl-4-hydroxyphenyl)propionate]methane, 3,9-bis[2-(3-(3-tert-butyl-4-hydroxy-5-methylphenyl)-propionyloxy)-1,1-dimethylethyl]-2,4,8,10-tetraoxaspiro [5.5]undecane, and the like. The amine-based antioxidants include phenyl-α-naphthylamine, phenyl-β-naphthylamine, diphenylamine, p-hydroxyphenyl-β-naphthylamine, and the like. The organosulfur-based antioxidants include dilauryl-3,3'-thiodipropionate, dimyristyl-3,3'-thiodipropionate, distearyl-3,3'-thiodipropionate, pentaerythrityltetrakis(3-laurylthiopropionate), ditridecyl-3,3'-thiodipropionate, 2-mercaptobenzimidazole, and the like. The phosphorus-based antioxidants include triphenylphosphite, tris(2,4-di-tert-butylphenyl)phosphite, and the like. Among these antioxidants, the phenol-based antioxidants are preferred, and dibutylhydroxytoluene (BHT) is more preferred, from the viewpoint of being inexpensive and readily available.

The amount of the antioxidant is from 0.001 to 5 parts by mass, preferably from 0.01 to 1.0 part by mass, and more preferably from 0.05 to 0.5 parts by mass, based on 100 parts by mass of the polyalkylene oxide. When the amount of the antioxidant is less than 0.001 parts by mass, not only the unreacted radical initiator remains in large amounts, so that the lowering of the molecular weight progresses too far, thereby making it difficult to control to an intended molecular weight, but also there is a risk of giving disadvantageous influences to storage stability after the treatment. In addition, when the amount of the antioxidant exceeds 5 parts by mass, an effect which matches its amount used is not found, and there is also a risk of generating coloration depending upon the kinds of the antioxidant.

In addition, the amount of the antioxidant is preferably from 0.1 to 10 times by mass, more preferably from 1 to 5 times by mass, and even more preferably from 2 to 4 times by mass, of the amount of the radical initiator used, from the viewpoint of the amount of radicals generated by the above-mentioned radical initiator.

The treatment apparatus usable in the method of the present invention is not particularly limited, so long as the treatment apparatus is capable of heating a polyalkylene oxide in an aliphatic hydrocarbon solvent, and thereafter removing the solvent. The treatment apparatus includes, for example, small-scaled apparatus such as separable flasks; medium-scaled and large-scaled apparatus include agitated trough dryers, and the like.

The viscosity-average molecular weight of the medium-molecular weight polyalkylene oxide obtainable by the method of the present invention is from 100,000 to 2,500,000, and preferably from 300,000 to 2,000,000. The viscosity-average molecular weight of the medium-molecular weight polyalkylene oxide obtained can be adjusted by the amount of the radical initiator, the heat treatment time, the heating temperature, and the like.

EXAMPLES

The present invention will be specifically described hereinbelow by the Examples, without intending to limit the scope of the present invention to the following Examples.

Here, the properties of the samples obtained in Examples and Comparative Examples were evaluated by the following methods.

(1) Aqueous Solution Viscosity

A 1-L beaker is charged with 475 g of ion-exchanged water, and 25 g of a sample is supplied thereto while stirring with a flat plate having a width of 80 mm and a length of 25 mm under the conditions of a tip end peripheral speed of 1.0 m/s. The stirring is continued for 3 hours to prepare an aqueous 5.0% by mass solution. In addition, similarly, as for an aqueous 0.5% solution, a 1-L beaker is charged with 497.5 g, and 2.5 g of a sample is supplied thereto while stirring with a flat plate having a width of 80 mm and a length of 25 mm under the conditions of a tip end peripheral speed of 1.0 m/s. The stirring is continued for 3 hours to prepare the aqueous solution.

A viscosity of the aqueous solution obtained is measured by immersing the aqueous solution including the above-mentioned beaker in a thermostat held at 25° C. for 30 minutes or more, with a B-type rotary viscometer at a rotational speed of 12 r/min, 3 minutes, at 25° C. (aqueous solution viscosity A). A rotor used in the measurement is Rotor No. 1 when the viscosity to be measured is less than 500 mPa·s, a rotor used is Rotor No. 2 when the viscosity to be measured is 500 mPa·s or more and less than 2,500 mPa·s, and a rotor used is Rotor No. 3 when the viscosity to be measured is 2,500 mPa·s or more and less than 10,000 mPa·s, and a rotor used is Rotor No. 4 when the viscosity to be measured is 10,000 mPa·s or more and less than 100,000.

(2) Viscosity-Average Molecular Weight

A viscosity-average molecular weight is calculated from the values of limiting viscosity with an Ostwald's viscometer using the Staudinger formula.

(3) Viscosity Retention Rate

An aqueous 5.0% by mass solution is prepared in the same manner as in (1), except that a powder sample used in the above (1) is stored at 40° C. for 30 days, and a sample on the 30th day after passage of a storage period is used. The measured viscosity of the aqueous solution is referred to as an aqueous solution viscosity B.

A viscosity retention rate after a 30-day storage is calculated from the following formula, using both of the aqueous solution viscosities. Here, if a viscosity retention rate is 80% or more, it can be judged that the lowering of the molecular weight is inhibited.

$$\text{Viscosity Retention Rate} = \frac{\text{Aqueous Solution Viscosity } B}{\text{Aqueous Solution Viscosity } A} \times 100$$

Example 1

A 500-ml separable flask was charged with 50 g of a polyethylene oxide having a viscosity-average molecular weight of 4,500,000, polymerized with an organozinc/alcohol-based catalyst, and 230 g of n-hexane. While aerating a 1% by volume oxygen-containing nitrogen (1% $O_2$—$N_2$) at a rate of 45 mL/min with stirring, an internal temperature was raised to 45° C. Next, 0.005 g of 2,2'-azobis(2,4'-dimethylvaleronitrile) was added thereto as a radical initiator, and the contents were stir-mixed at 45° C. for 5 hours to carry out a heat treatment. At this time, a dissolved oxygen concentration in the solvent n-hexane was 2.9 mg/L. After the termination of the heat treatment, 0.05 g of dibutylhydroxytoluene was added as an antioxidant to a treated solution, and n-hexane was distilled off, i.e. removed, to give a white powder. This powder was analyzed, and consequently had an aqueous solution viscosity of 16,700 mPa·s in an aqueous 5.0% by mass solution, and a viscosity-average molecular weight of 1,400,000.

This powder was stored in a thermostat at 40° C., and an aqueous solution viscosity with the passage of time was measured. Consequently, the powder showed a viscosity retention rate of 90% after a 30-day storage.

Example 2

The same procedures as in Example 1 were carried out except that the amount of 2,2'-azobis(2,4'-dimethylvaleronitrile) was changed from 0.005 g to 0.025 g, to give a white powder. This powder was analyzed, and consequently, the powder had an aqueous solution viscosity of 835 mPa·s in an aqueous 5.0% by mass solution, and a viscosity-average molecular weight of 500,000.

This powder was stored in a thermostat at 40° C., and an aqueous solution viscosity with the passage of time was measured. Consequently, the powder showed a viscosity retention rate of 88% after a 30-day storage.

Example 3

The same procedures as in Example 1 were carried out except that the amount of 2,2'-azobis(2,4'-dimethylvaleronitrile) was changed from 0.005 g to 0.250 g, to give a white powder. This powder was analyzed, and consequently, the powder had an aqueous solution viscosity of 167 mPa·s in an aqueous 5.0% by mass solution, and a viscosity-average molecular weight of 300,000.

This powder was stored in a thermostat at 40° C., and an aqueous solution viscosity with the passage of time was measured. Consequently, the powder showed a viscosity retention rate of 83% after a 30-day storage.

Example 4

The same procedures as in Example 2 were carried out except that the heat treatment time was changed from 5 hours to 3 hours, to give a white powder. This powder was analyzed, and consequently, the powder had an aqueous solution viscosity of 6,270 mPa·s in an aqueous 5.0% by mass solution, and a viscosity-average molecular weight of 1,000,000.

This powder was stored in a thermostat at 40° C., and an aqueous solution viscosity with the passage of time was measured. Consequently, the powder showed a viscosity retention rate of 88% after a 30-day storage.

Example 5

The same procedures as in Example 2 were carried out except that the heat treatment time was changed from 5 hours to 1 hour, to give a white powder. This powder was analyzed, and consequently, the powder had an aqueous solution viscosity of 30,500 mPa·s in an aqueous 5.0% by mass solution, and a viscosity-average molecular weight of 1,750,000.

This powder was stored in a thermostat at 40° C., and an aqueous solution viscosity with the passage of time was measured. Consequently, the powder showed a viscosity retention rate of 82% after a 30-day storage.

Example 6

The same procedures as in Example 2 were carried out except that a polyethylene oxide having a viscosity-average molecular weight of 8,500,000 was used in place of the polyethylene oxide having a viscosity-average molecular weight of 4,500,000, to give a white powder. This powder was analyzed, and consequently, the powder had an aqueous solution viscosity of 2,040 mPa·s in an aqueous 5.0% by mass solution, and a viscosity-average molecular weight of 700,000.

This powder was stored in a thermostat at 40° C., and an aqueous solution viscosity with the passage of time was measured. Consequently, the powder showed a viscosity retention rate of 90% after a 30-day storage.

Example 7

The same procedures as in Example 2 were carried out except that a polyethylene oxide having a viscosity-average molecular weight of 5,200,000 was used in place of the polyethylene oxide having a viscosity-average molecular weight of 4,500,000, and that the heat treatment temperature was changed from 45° C. to 35° C., to give a white powder. This powder was analyzed, and consequently, the powder had an aqueous solution viscosity of 38,200 mPa·s in an aqueous 5.0% by mass solution, and a viscosity-average molecular weight of 1,900,000.

This powder was stored in a thermostat at 40° C., and an aqueous solution viscosity with the passage of time was measured. Consequently, the powder showed a viscosity retention rate of 85% after a 30-day storage.

Example 8

The same procedures as in Example 7 were carried out except that the heat treatment temperature was changed from 35° C. to 40° C., to give a white powder. This powder was analyzed, and consequently, the powder had an aqueous solution viscosity of 8,240 mPa·s in an aqueous 5.0% by mass solution, and a viscosity-average molecular weight of 1,100,000.

This powder was stored in a thermostat at 40° C., and an aqueous solution viscosity with the passage of time was measured. Consequently, the powder showed a viscosity retention rate of 88% after a 30-day storage.

Example 9

The same procedures as in Example 7 were carried out except that the heat treatment temperature was changed from 35° C. to 45° C., to give a white powder. This powder was analyzed, and consequently, the powder had an aqueous solution viscosity of 1,470 mPa·s in an aqueous 5.0% by mass solution, and a viscosity-average molecular weight of 600,000.

This powder was stored in a thermostat at 40° C., and an aqueous solution viscosity with the passage of time was measured. Consequently, the powder showed a viscosity retention rate of 92% after a 30-day storage.

Example 10

The same procedures as in Example 7 were carried out except that the heat treatment temperature was changed from 35° C. to 50° C., to give a white powder. This powder was analyzed, and consequently, the powder had an aqueous solution viscosity of 335 mPa·s in an aqueous 5.0% by mass solution, and a viscosity-average molecular weight of 400,000.

This powder was stored in a thermostat at 40° C., and an aqueous solution viscosity with the passage of time was measured. Consequently, the powder showed a viscosity retention rate of 91% after a 30-day storage.

Example 11

A 500-ml separable flask was charged with 50 g of a polyethylene oxide having a viscosity-average molecular weight of 8,500,000, polymerized with an organozinc/alcohol-based catalyst, and 230 g of n-hexane. While aerating a 0.1% by volume oxygen-containing nitrogen (0.1% $O_2$—$N_2$) at a rate of 45 mL/min with stirring, an internal temperature was raised to 45° C. Next, 0.025 g of 2,2'-azobis(2,4'-dimethylvaleronitrile) was added thereto, and the contents were stir-mixed at 45° C. for 5 hours to carry out a heat treatment. At this time, a dissolved oxygen concentration in the solvent n-hexane was 0.5 mg/L. After the termination of the heat treatment, 0.05 g of dibutylhydroxytoluene was added to a treated solution, and n-hexane was distilled off, to give a white powder. This powder was analyzed, and consequently had an aqueous solution viscosity of 6,230 mPa·s in an aqueous 5.0% by mass solution, and a viscosity-average molecular weight of 1,000,000.

This powder was stored in a thermostat at 40° C., and an aqueous solution viscosity with the passage of time was measured. Consequently, the powder showed a viscosity retention rate of 88% after a 30-day storage.

Comparative Example 1

A 500-ml separable flask was charged with 50 g of a polyethylene oxide having a viscosity-average molecular weight of 8,500,000, polymerized with an organozinc/alcohol-based catalyst, and 230 g of n-hexane. While aerating pure nitrogen at a rate of 45 mL/min with stirring, an internal temperature was raised to 45° C. Next, 0.025 g of 2,2'-azobis (2,4'-dimethylvaleronitrile) was added thereto, and the contents were stir-mixed at 45° C. for 5 hours to carry out a heat treatment. At this time, a dissolved oxygen concentration in the solvent n-hexane was 0.0 mg/L. After the termination of the heat treatment, 0.05 g of dibutylhydroxytoluene was added to a treated solution, and n-hexane was distilled off, to give a white powder. This powder was analyzed. Since a measurement could not be obtained with an aqueous 5.0% by mass solution, a measurement was made with an aqueous 0.5% by mass solution, and the powder consequently had an aqueous solution viscosity of 285 mPa·s in an aqueous 0.5% by mass solution, and a molecular weight only lowered to as far as a viscosity-average molecular weight of 4,200,000.

Comparative Example 2

The same procedures as in Example 9 were carried out except that the amount of 2,2'-azobis(2,4'-dimethylvaleronitrile) was changed from 0.025 g to 0.0004 g, to give a white powder. This powder was analyzed. Since a measurement could not be obtained with an aqueous 5.0% by mass solution, a measurement was made with an aqueous 0.5% by mass solution, and the powder consequently had an aqueous solution viscosity of 295 mPa·s in an aqueous 0.5% by mass solution, and a molecular weight only lowered to as far as a viscosity-average molecular weight of 4,200,000.

Comparative Example 3

The same procedures as in Example 9 were carried out except that the amount of 2,2'-azobis(2,4'-dimethylvaleronitrile) was changed from 0.025 g to 0.750 g, and that the heat treatment time was changed from 5 hours to 1 hour, to give a white powder. This powder was analyzed, and consequently had an aqueous solution viscosity of 3,120 mPa·s in an aqueous 5.0% by mass solution, and a viscosity-average molecular weight of 800,000.

This powder was stored in a thermostat at 40° C., and an aqueous solution viscosity with the passage of time was measured. Consequently, the powder only showed a viscosity retention rate of 30% after a 30-day storage.

Comparative Example 4

The same procedures as in Example 7 were carried out except that the heat treatment temperature was changed from 35° C. to 25° C., to give a white powder. This powder was analyzed. Since a measurement could not be obtained with an aqueous 5.0% by mass solution, a measurement was made with an aqueous 0.5% by mass solution, and the powder consequently had an aqueous solution viscosity of 410 mPa·s in an aqueous 0.5% by mass solution, and a molecular weight only lowered to as far as a viscosity-average molecular weight of 4,800,000.

Comparative Example 5

A 500-ml separable flask was charged with 50 g of a polyethylene oxide having a viscosity-average molecular weight of 8,500,000, polymerized with an organozinc/alcohol-based catalyst, and 230 g of n-hexane. While aerating a 1.0% by volume oxygen-containing nitrogen (1% $O_2$—$N_2$) at a rate of 45 mL/min with stirring, an internal temperature was raised to 45° C. Next, 0.025 g of 2,2'-azobis(2,4'-dimethylvaleronitrile) was added thereto, and the contents were stir-mixed at 45° C. for 5 hours to carry out a heat treatment.

At this time, a dissolved oxygen concentration in the solvent n-hexane was 2.9 mg/L. After the termination of the heat treatment, and n-hexane was distilled off without adding dibutylhydroxytoluene to a treated solution, to give a white powder. This powder was analyzed, and consequently had an aqueous solution viscosity of 50 mPa·s in an aqueous 5.0% by mass solution, and a viscosity-average molecular weight of 200,000.

This powder was stored in a thermostat at 40° C., and an aqueous solution viscosity with the passage of time was measured. Consequently, the powder only showed a viscosity retention rate of 17% after a 30-day storage.

TABLE 1

|  | Viscosity-Average Molecular Weight Before Heat Treatment (×10$^4$) | Amount of Radical Initiator (g) | Dissolved Oxygen Concentration in Solvent (mg/L) | Heat Treatment Conditions Temp. (° C.) | Heat Treatment Conditions Time (hr) | Amount of Antioxidant (g) | Aqueous Solution Viscosity [5.0%] (mPa·S) | Viscosity-Average Molecular Weight (×10$^4$) | Viscosity Retention Rate at 40° C. After 30-Day Storage (%) |
|---|---|---|---|---|---|---|---|---|---|
| Ex. 1 | 450 | 0.005 | 2.9 | 45 | 5 | 0.05 | 16,700 | 140 | 90 |
| Ex. 2 | 450 | 0.025 | 2.9 | 45 | 5 | 0.05 | 835 | 50 | 88 |
| Ex. 3 | 450 | 0.250 | 2.9 | 45 | 5 | 0.05 | 167 | 30 | 83 |
| Ex. 4 | 450 | 0.025 | 2.9 | 45 | 3 | 0.05 | 6,270 | 100 | 88 |
| Ex. 5 | 450 | 0.025 | 2.9 | 45 | 1 | 0.05 | 30,500 | 175 | 82 |
| Ex. 6 | 850 | 0.025 | 2.9 | 45 | 5 | 0.05 | 2,040 | 70 | 90 |
| Ex. 7 | 520 | 0.025 | 2.9 | 35 | 5 | 0.05 | 38,200 | 190 | 85 |
| Ex. 8 | 520 | 0.025 | 2.9 | 40 | 5 | 0.05 | 8,240 | 110 | 88 |
| Ex. 9 | 520 | 0.025 | 2.9 | 45 | 5 | 0.05 | 1,470 | 60 | 92 |
| Ex. 10 | 520 | 0.025 | 2.9 | 50 | 5 | 0.05 | 335 | 40 | 91 |
| Ex. 11 | 850 | 0.025 | 0.5 | 45 | 5 | 0.05 | 6,230 | 100 | 88 |
| Comp. Ex. 1 | 850 | 0.025 | 0.0 | 45 | 5 | 0.05 | 285 [0.5%] | 420 | — |
| Comp. Ex. 2 | 520 | 0.0004 | 2.9 | 45 | 5 | 0.05 | 295 [0.5%] | 420 | — |
| Comp. Ex. 3 | 520 | 0.750 | 2.9 | 45 | 1 | 0.05 | 3,120 | 80 | 30 |
| Comp. Ex. 4 | 520 | 0.025 | 2.9 | 25 | 5 | 0.05 | 410 [0.5%] | 480 | — |
| Comp. Ex. 5 | 850 | 0.025 | 2.9 | 45 | 5 | 0.00 | 50 | 20 | 17 |

It can be seen from the results of Example 6 and Comparative Example 1 that when a dissolved oxygen in the slurry is lower than 0.5 mg/L, the effect of lowering its molecular weight can be hardly obtained.

It can be seen from the results of Example 9 and Comparative Example 2 that when the amount of the radical initiator is smaller than 0.001 parts by mass, based on 100 parts by mass of the polyalkylene oxide, the effect of lowering its molecular weight can be hardly obtained.

It can be seen from the results of Example 9 and Comparative Example 3, when the amount of the radical initiator is greater than 1 part by mass, based on 100 parts by mass of the polyalkylene oxide, a viscosity retention rate at 40° C. after a 30-day storage is worsened.

It can be seen from the results of Example 9, Example 7 and Comparative Example 4, when the treatment temperature is lower than 30° C., the effect of lowering its molecular weight can be hardly obtained.

It can be seen from the results of Example 6 and Comparative Example 5, when the amount of the antioxidant is smaller than 0.001 parts by mass, based on 100 parts by mass of the polyalkylene oxide, the lowering of the molecular weight undesirably progresses too far, so that not only a viscosity after solvent distillation becomes too low but also a viscosity retention rate after a 30-day storage is worsened.

Here, with regard to Comparative Examples 1, 2 and 4, measurements could not be obtained with an aqueous 5.0% by mass solution, so that a viscosity retention rate at 40° C. after a 30-day storage could not be calculated.

INDUSTRIAL APPLICABILITY

The medium-molecular weight polyalkylene oxide obtainable by the method of the present invention can be used in thickeners for making paper, ceramic binders, aids in suspension polymerization, raw materials for pharmaceutical formulations, and the like.

The invention claimed is:

1. A method for producing a medium-molecular weight polyalkylene oxide, the method comprising
   heat-treating a polyalkylene oxide having a viscosity-average molecular weight of 3,000,000 or more at a temperature of from 30 to 50° C. in an aliphatic hydrocarbon solvent comprising dissolved oxygen at a concentration of 0.5 mg/L or more, in the presence of a radical initiator in an amount of from 0.001 to 1 part by mass, based on 100 parts by mass of the polyalkylene oxide, and
   thereafter adding an antioxidant in an amount of from 0.001 to 5 parts by mass, based on 100 parts by mass of the polyalkylene oxide to remove the solvent, thereby obtaining the medium-molecular weight polyalkylene oxide, which has a viscosity-average molecular weight of from 100,000 to 2,500,000,
   wherein the radical initiator has a 10-hour half-life temperature of 70° C. or lower and is at least one selected from the group consisting of an azonitrile, an azoamidine, an azoimidazoline, a sulfur-comprising compound, an oxidizing agent, and an organometallic compound.

2. The method according to claim 1, wherein the radical initiator is at least one selected from the group consisting of 2,2'-azobis(4-methoxy-2,4'-dimethylvaleronitrile), 2,2'-azobis-(2,4'-dimethylvaleronitrile), 2,2'-azobis[N-(2-carboxymethyl)-2-methyl-propionamidine]tetrahydrate, 2,2'-azobis(2-amidinopropane)dihydrochloride, 2,2'-azobis[2-(2-imidazolin-2-yl)propane]dihydrochloride, 2,2'-azobis[2-(2-imidazolin-2-yl)propane]disulfate dihydrate, tetramethylthiuram disulfide, potassium permanganate, alkylaluminum, and alkylzinc.

3. The method according to claim 1, wherein the antioxidant is at least one selected from the group consisting of a phenol-based antioxidant, an amine-based antioxidant, an organosulfur-based antioxidant, and a phosphorus-based antioxidant.

4. The method according to claim 1, wherein the polyalkylene oxide having a viscosity-average molecular weight of 3,000,000 or more is a polyethylene oxide or an ethylene oxide/propylene oxide copolymer.

5. The method according to claim 2, wherein the antioxidant is at least one selected from the group consisting of a phenol-based antioxidant, an amine-based antioxidant, an organosulfur-based antioxidant, and a phosphorus-based antioxidant.

6. The method according to claim 2, wherein the polyalkylene oxide having a viscosity-average molecular weight of 3,000,000 or more is a polyethylene oxide or an ethylene oxide/propylene oxide copolymer.

7. The method according to claim 3, wherein the polyalkylene oxide having a viscosity-average molecular weight of 3,000,000 or more is a polyethylene oxide or an ethylene oxide/propylene oxide copolymer.

8. The method according to claim 1, wherein the radical initiator is an azonitrile.

9. The method according to claim 1, wherein the aliphatic hydrocarbon solvent comprises from 5 to 8 carbon atoms.

* * * * *